US00PP29582P2

(12) United States Plant Patent
van Noort

(10) Patent No.: US PP29,582 P2
(45) Date of Patent: Aug. 7, 2018

(54) ***GERANIUM* PLANT NAMED 'NOGETWO'**

(50) Latin Name: *Geranium wallichianum*
Varietal Denomination: Nogetwo

(71) Applicant: Marco van Noort, Warmond (NL)

(72) Inventor: Marco van Noort, Warmond (NL)

(73) Assignee: MARCO VAN NOORT BREEDING BV, Warmond (NL)

( * ) Notice: Subject to any disclaimer, the term of this patent is extended or adjusted under 35 U.S.C. 154(b) by 0 days.

(21) Appl. No.: 15/530,503

(22) Filed: Jan. 23, 2017

(51) Int. Cl.
*A01H 5/02* (2018.01)

(52) U.S. Cl.
USPC ..... Plt./324
CPC ..... *A01H 5/0277* (2013.01)

(58) Field of Classification Search
USPC ..... Plt./324, 325, 332
CPC ..... A01H 5/0277
See application file for complete search history.

*Primary Examiner* — Kent L Bell
(74) *Attorney, Agent, or Firm* — Penny J. Aguirre

(57) ABSTRACT

A new cultivar of *Geranium wallichianum*, 'Nogetwo', characterized by its compact plant habit, its flowers that are dark purple-blue in color with overlapping petals to produce a circular shape, its long blooming season; blooming from June to late fall in The Netherlands, and its resistance to bacterial leaf spot and botrytis blossom blight.

2 Drawing Sheets

Botanical classification: *Geranium wallichianum.*
Cultivar designation: 'Nogetwo'.

BACKGROUND OF THE INVENTION

The present invention relates to a new and distinct cultivar of *Geranium* plant, botanically known as *Geranium wallichianum* 'Nogetwo' and will be referred to hereafter by its cultivar name, 'Nogetwo'. 'Nogetwo' is a new cultivar of herbaceous perennial grown for use as a garden plant.

'Nogetwo' arose from an on going breeding program conducted by the Inventor in Warmond, The Netherlands. The objectives of the breeding program is to develop new cultivars of *Geranium* with strong and compact plant habits, long flowering habits, unique flower colors and resistance to diseases and pests.

'Nogetwo' originated as a cross made by the Inventor in 2009 between unnamed and unpatented proprietary plants from the Inventor's breeding program as both the female and male parents. The new *Geranium* was selected as a single unique plant in July of 2010 from amongst the resulting seedling from the above cross.

Asexual propagation of the new cultivar was first accomplished by tissue culture using meristematic tissue under the direction of the Inventor in Otrobusy, Poland in May 2016. Asexual propagation by division and tissue culture has determined that the characteristics of the new cultivar are stable and are reproduced true to type in successive generations.

SUMMARY OF THE INVENTION

The following traits have been repeatedly observed and represent the characteristics of 'Nogetwo'. These attributes in combination distinguish 'Nogetwo' as a new and distinct cultivar of *Geranium.*

1. 'Nogetwo' exhibits a compact plant habit.
2. 'Nogetwo' exhibits flowers that are dark purple-blue in color with overlapping petals to produce a circular shape.
3. 'Nogetwo' exhibits a long blooming season; blooming from June to late fall in The Netherlands.
4. 'Nogetwo' exhibits resistance to bacterial leaf spot and botrytis blossom blight.

The female parent differs from 'Nogetwo' in having a less compact plant habit, flower petals that are not overlapping resulting in a more open flower shape, and a shorter flowering period. The male parent differs from 'Nogetwo' in having a less compact plant habit, in having a lighter flower color and in having flower petals that are not overlapping. 'Nogetwo' can be most closely compared to the cultivars 'Rainbow' (U.S. Plant Pat. No. 18,968) and 'Buxton's Variety' (not patented). 'Rainbow' is similar to 'Nogetwo' in having similar flower color. 'Rainbow' differs from 'Nogetwo' in having a less compact plant habit, flowers that are lighter in color, flower petals that are not overlapping, and a shorter blooming period. 'Buxton's Variety' is similar to 'Nogetwo' in having a similar blooming period. 'Buxton's Variety' differs from 'Nogetwo' in having a less compact plant habit and flowers that are lighter in color.

BRIEF DESCRIPTION OF THE DRAWINGS

The accompanying colored photographs illustrate the overall appearance and distinct characteristics of the new *Geranium*. The photographs were taken of one year-old plants of 'Nogetwo' as grown outdoors in a nursery bed in Warmond, The Netherlands.

The photograph in FIG. 1 provides a top view of 'Nogetwo' in bloom.

Figure 1:
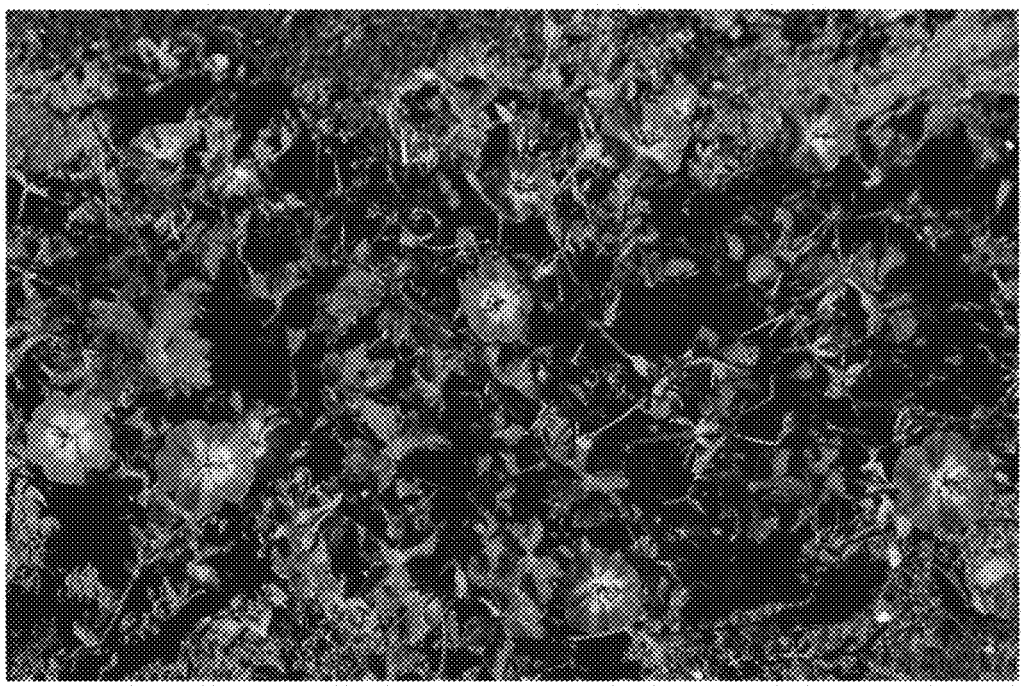
Figure 2:
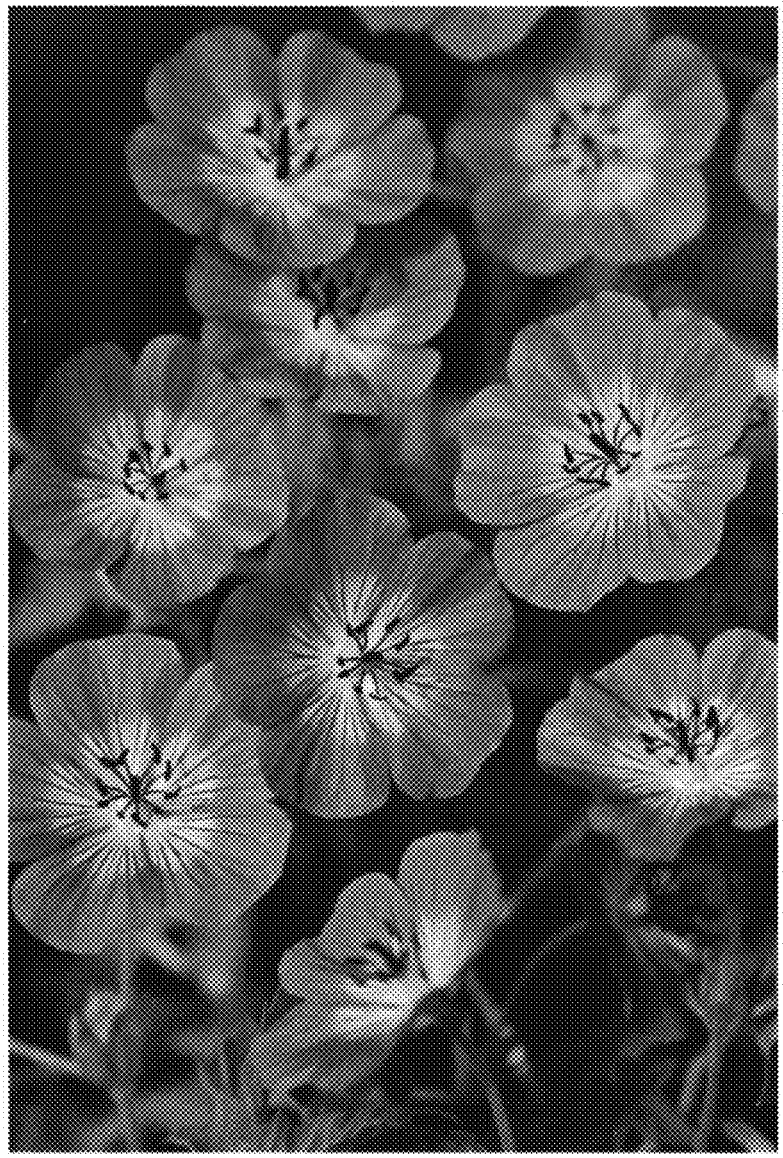

The photograph in FIG. 2 provides a close-up view of the flowers of 'Nogetwo'.

The colors in the photographs are as close as possible with the digital photography and printing techniques utilized and the color codes in the detailed botanical description accurately describe the colors of the new *Geranium.*

DETAILED BOTANICAL DESCRIPTION OF THE PLANT

The following is a detailed description of one year-old plants of the new cultivar as grown outdoors in a nursery bed in Warmond, The Netherlands. Plants were grown under average day temperatures of 14° C. to 30° C. and average night temperatures of 6° C. to 18° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—June to late fall in The Netherlands.
*Plant type.*—Herbaceous perennial.
*Plant habit.*—Compact mound, moderately spreading.
*Height and spread.*—Reaches about 35 cm in height and 45 cm in spread.
*Cold hardiness.*—At least to U.S.D.A. Zone 5.
*Diseases and pests.*—Resistance has been observed to bacterial leaf spot (*Xanthomonas pelargonii*) and botrytis blossom blight (*Botrytis cinerea*) and no pest problems have been observed.
*Root description.*—Fibrous roots extending from stout rootstock.
*Growth rate.*—Moderately vigorous.
*Growth habit.*—Strong.
*Propagation.*—Division and tissue culture.

Stem description:

*Stem size.*—Average of 14.5 cm in length and 2 mm in width.
*Stem shape.*—Round.
*Stem strength.*—Moderately strong.
*Stem color.*—Young upper surface 176A, young lower surface 151C, mature upper surface 175A, young lower surface 146C.
*Stem surface.*—Moderately glossy and moderately covered with short hairs, average of 1 mm in length and NN155D in color.
*Internode length.*—Average of 6.6 cm.
*Branching habit.*—Freely branched, average of 4 main branches, 12 lateral branches.

Foliage description:

*Leaf shape.*—Reniform (overall shape), deeply cleft with an average of five lobes.
*Leaf division.*—Simple.
*Leaf base.*—Hastate, lobes free to touching.
*Leaf apex.*—Acute.
*Leaf venation.*—Palmate, upper surface color; 137A to 137B, lower surface color; 147B to 147C.
*Leaf margins.*—Coarsely serrate.
*Leaf aspect.*—Average of 60° to petiole.
*Leaf lobes.*—Sinuses are deep, sinus orientation is convergent.
*Leaf attachment.*—Petiolate.
*Leaf arrangement.*—Opposite.
*Leaf surface.*—Upper surface non-rugose, lower surface moderately rugose, both surfaces are matte and pubescent, covered with short hairs an average of 1 mm in length and 155C in color, main and secondary veins are covered with short hairs; 0.75 mm in length and NN155D in color.
*Leaf color.*—Young upper surface; 143A, young lower surface; 138B, mature upper surface; 137A, dots 143C, mature lower surface; 147B.
*Leaf size.*—Average of 6.2 cm in length and 7 cm in width.
*Leaf quantity.*—Average of 6 (3 pairs) per lateral branch.
*Petioles.*—Average of 8.3 cm in length and 1.5 mm in width, upper surface color 181C, fading towards the base 145A, lower surface color 181C to 181D, fading towards the base 145A, both surfaces are moderately glossy, densely covered with short hairs an average of 1 mm in length and NN155D, high strength.
*Stipules.*—2 leafy stipules, present at the base of the leaves, broad ovate in shape, apex is broadly acute, average of 1.4 cm in length and 1.2 cm in width, both surfaces 145A, margined 63C, dried N199B to 200D.

Flower description:

*Inflorescence type.*—Single, rotate, arranged in pairs.
*Lastingness of flowers.*—About 7 days, self cleaning.
*Flower size.*—Average of 4.2 cm and diameter, 1.2 cm in depth.
*Flower fragrance.*—None.
*Flower number.*—Average of 8 flower per lateral stem.
*Flower aspect.*—Primarily upward.
*Flower type.*—Rotate.
*Flower bud size.*—An average of 1.3 cm in length, up to 6 mm in width.
*Flower bud color.*—143A, axially striped 144B, fading to base 144B.
*Flower bud shape.*—Ovate.
*Flower bud quantity.*—Average of 40.
*Flower bud texture.*—Densely covered with short hairs an average of 1 mm in length and NN155D in color.
*Petal number.*—5.
*Petal shape.*—Inverted deltoid to obcordate.
*Petal base.*—Cuneate.
*Petal apex.*—Broad retuse.
*Petal margins.*—Entire, very low undulation.
*Petal size.*—Average of 2.1 cm in length and width.
*Petal color.*—When opening and fully open upper surface; N81B, fading towards the margins N88B, base 76A, petal veins 71A, when opening and fully open lower surface; N82B, fading towards the margins N87A, base 76A, petal veins 72A.
*Petal surface.*—Glabrous, matte, velvety.
*Calyx form.*—Cylindrical.
*Calyx size.*—Average of 7 mm in length and 2.6 cm in width.
*Sepal numbers.*—Average of 5.
*Sepal shape.*—Elliptic.
*Sepal margin.*—Entire.
*Sepal size.*—Average of 1.4 cm length, 4 mm in width.
*Sepal surface.*—Upper surface glabrous, smooth, moderately glossy, lower surface glabrous, smooth, matte, main veins are densely covered with short hairs average of 1 mm in length, NN155D in color.
*Sepal apex.*—Mucronate.
*Sepal base.*—Cuneate.

*Sepal color*.—Opening and fully open upper surface; 144A, margined NN144A, when opening lower surface; 143C, veined 144A, fully open lower surface 143C, veins 144A.

*Peduncle*.—Average of 11 cm in length and 1.5 mm in diameter, moderately to strong, held at about a 32.5° angle relative to lateral branch, upper side 177A in color, lower side 146B to 146C in color, pubescent surface, densely covered with short hairs, average of 1.25 mm in length and NN155D in color.

*Pedicel*.—Average of 4.5 cm in length and 1 mm in diameter, moderately to strong, held at about a 25° angle relative to lateral branch, upper side 177D in color, lower side 146D in color, pubescent surface, densely covered with short hairs, average of 1 mm in length and NN155D in color.

*Floral bracts*.—Four bracts are placed at the top of each peduncle, elliptic in shape, concave, average of 1.5 cm in length, 7 mm in width, entire margin, mucronate apex, cuneate base, upper surface smooth and glabrous, lower surface densely covered with short hairs average of 0.75 mm in length, NN155D in color, both surfaces of bracts are 144C in color, margins and tip 184D in color.

Reproductive organs:

*Gynoecium*.—Pistil; 1, average of 7 mm in length, stigmas; 5, decurrent, 4 mm in length, 0.75 mm in diameter and N186C in color, style; average of 5 mm in length and 143B in color, ovary is 143A in color.

*Androcoecium*.—Stamens; 10, anthers; dorsifixed, broad oblong in shape, 2.5 mm in length, 1 mm in width and 203C in color, filaments; 9 mm in length, N186C, fading towards the base to NN155D, pollen is abundant in quantity and N187A and 202B in color.

*Fruit/seeds*.—No fruit or seeds detected to date.

It is claimed:

1. A new and distinct cultivar of *Geranium* plant named 'Nogetwo' as herein illustrated and described.

* * * * *